United States Patent [19]

Abele et al.

[11] Patent Number: 4,772,093
[45] Date of Patent: Sep. 20, 1988

[54] FIBER-OPTIC IMAGE-CARRYING DEVICE

[75] Inventors: John E. Abele, Concord, Mass.; George E. Strom, North Kingstown, R.I.; James F. Hopkins, Marlboro, Mass.; Thomas A. Jellison, Framingham, Mass.; Alice H. Pincus, Andover, Mass.

[73] Assignee: Microvasive, Inc., Milford, Mass.

[21] Appl. No.: 917,915

[22] Filed: Oct. 10, 1986

Related U.S. Application Data

[63] Continuation-in-part of Ser. No. 808,043, Dec. 12, 1985, abandoned, which is a continuation-in-part of Ser. No. 786,893, Oct. 11, 1985, abandoned.

[51] Int. Cl.$^4$ .......................... G02B 6/06; A61B 1/00; A61N 7/00
[52] U.S. Cl. ............................ 350/96.25; 350/96.24; 128/5
[58] Field of Search ............... 350/96.24, 96.25, 96.26, 350/96.23, 96.34; 65/3.11; 128/4, 5, 6, 397, 398; 427/54.1, 36, 163

[56] References Cited

U.S. PATENT DOCUMENTS

| | | | |
|---|---|---|---|
| 2,825,260 | 3/1958 | O'Brien | 88/1 |
| 3,004,368 | 10/1961 | Hicks, Jr. | 49/79 |
| 3,010,357 | 11/1961 | Hirschowitz | 88/1 |
| 3,016,785 | 1/1962 | Kapany | 88/1 |
| 3,131,690 | 5/1964 | Innis et al. | 128/23 |
| 3,145,249 | 8/1964 | Meltzer | 88/1 |
| 3,236,710 | 2/1966 | Curtiss | 156/167 |
| 3,253,500 | 5/1966 | Hicks, Jr. | 88/1 |
| 3,417,746 | 12/1968 | Moore et al. | 128/6 |
| 3,498,286 | 3/1970 | Polanyi et al. | 128/2 |
| 3,504,984 | 4/1970 | Bush | 356/256 |
| 3,554,721 | 1/1971 | Gardner | 65/4 |
| 3,556,635 | 1/1971 | Schrenk et al. | 350/96.10 |
| 3,581,738 | 6/1971 | Moore | 128/6 |
| 3,589,793 | 6/1971 | Curtiss | 350/96.10 |
| 3,624,816 | 11/1971 | Strack et al. | 350/96.10 |
| 3,649,098 | 3/1972 | Suverison | 350/96.10 |
| 3,653,739 | 4/1972 | Strack | 350/96.10 |
| 3,669,772 | 6/1972 | Strack | 156/15 |
| 3,674,452 | 7/1972 | Strack | 65/4 |
| 3,690,853 | 9/1972 | Law | 65/4 |
| 3,691,001 | 9/1972 | Takahashi et al. | 161/96 |
| 3,807,390 | 4/1974 | Ostrowski et al. | 128/2.05 R |

(List continued on next page.)

FOREIGN PATENT DOCUMENTS

| | | |
|---|---|---|
| 0084216 | 7/1983 | European Pat. Off. . |
| 0097934 | 1/1984 | European Pat. Off. . |
| 0116910 | 8/1984 | European Pat. Off. . |
| 0121215 | 10/1984 | European Pat. Off. . |
| 2719504 | 11/1978 | Fed. Rep. of Germany . |
| 3014407 | 10/1980 | Fed. Rep. of Germany . |
| 2436405 | 4/1980 | France . |
| 0924774 | 5/1963 | United Kingdom . |
| 0969941 | 9/1964 | United Kingdom . |
| 1357156 | 6/1974 | United Kingdom . |

OTHER PUBLICATIONS

Ansel et al. "An Overview of Ultra Violet Light (UV) Curing Systems Used as Optical Wave Guide Coatings", DESOTO, Inc. pp, 1–28.

(List continued on next page.)

*Primary Examiner*—William L. Sikes
*Assistant Examiner*—Akm E. Ullah

[57] ABSTRACT

An elongated image-carrying member that enables microendoscopy to be practiced using normal-sized catheters, includes a drawn, fused, central multi-fiber micro-unit of about 0.5 mm diameter, having about 2,000 glass fibers in coherent array, with a polymeric coating bonded to its pristine as-drawn outer surface. This combination achieves sufficient flexibility and optical qualities to enable effective use to provide vision for inspection of small passages and ducts. Flexible image-carrying members having diameter of 0.5 millimeter or less and catheters of diameter of 3 mm or less incorporating such members and effective working channels are achievable. For vision in remote areas, the micro-unit is employed with a substantially spherical lens with an ocular system for providing a focus range from less than about 2 mm to infinity and having resolution of detail down to the order of about 0.001 inch. The micro-optical member may be employed with a handpiece in a vision system, the micro-optical member being joined to the handpiece by a detachable connector having a stepped structure for precise alignment between the handle and the micro-optical member. By application of a relatively thin coating containing an opaque constituent to the as drawn micro-unit, degradation of the image and avoidance of artifacts caused by wave guiding effect are avoided. Devices with varying bend radiuses are also shown.

13 Claims, 7 Drawing Sheets

U.S. PATENT DOCUMENTS

| | | | |
|---|---|---|---|
| 3,813,322 | 5/1974 | Vazirani | 204/159.15 |
| 3,830,667 | 8/1974 | Carpenter | 156/155 |
| 3,901,674 | 8/1975 | Strack et al. | 65/3 |
| 3,902,880 | 9/1975 | Strack | 65/4 |
| 3,930,103 | 12/1975 | Chimura et al. | 428/361 |
| 3,937,558 | 2/1976 | Mukai et al. | 350/96.10 |
| 3,948,251 | 4/1976 | Hosono | 128/4 |
| 3,981,706 | 9/1976 | Strack | 65/4 A |
| 4,009,382 | 2/1977 | Nath | 240/1 LP |
| 4,076,510 | 2/1978 | Mracek et al. | 65/3 A |
| 4,086,919 | 5/1978 | Bullard | 128/11 |
| 4,097,258 | 6/1978 | Horikawa et al. | 65/31 |
| 4,125,644 | 11/1978 | Ketley et al. | 427/36 |
| 4,139,260 | 2/1979 | Bouygues et al. | 350/96.22 |
| 4,168,109 | 9/1979 | Dumire | 350/96.22 |
| 4,246,299 | 1/1981 | Ohis | 427/54.1 |
| 4,279,466 | 7/1981 | Makuch et al. | 350/96.21 |
| 4,279,468 | 7/1981 | Turley et al. | 350/96.21 |
| 4,279,469 | 7/1981 | Forman | 350/96.20 |
| 4,300,816 | 11/1981 | Snitzer et al. | 350/96.33 |
| 4,311,726 | 1/1982 | Hacker | 427/54.1 |
| 4,312,564 | 1/1982 | Cefarelli et al. | 350/96.22 |
| 4,324,575 | 4/1982 | Levy | 65/3.11 |
| 4,330,169 | 5/1982 | Kantor | 350/9 |
| 4,341,439 | 7/1982 | Hodge | 350/96.22 |
| 4,388,093 | 6/1983 | Kimura et al. | 65/3.11 |
| 4,389,089 | 6/1983 | Strack | 350/96.21 |
| 4,396,645 | 8/1983 | Kimura et al. | 427/163 |
| 4,421,383 | 12/1983 | Carlsen | 350/96.21 |
| 4,461,841 | 7/1984 | Harada et al. | 501/37 |
| 4,472,019 | 9/1984 | Bishop et al. | 350/96.30 |
| 4,472,021 | 9/1984 | Ansel et al. | 350/96.23 |
| 4,474,174 | 10/1984 | Petruzzi | 128/4 |
| 4,482,204 | 11/1984 | Blyler, Jr. et al. | 350/96.34 |
| 4,483,585 | 11/1984 | Takami | 350/96.24 |
| 4,494,823 | 1/1985 | Yoshida et al. | 350/96.22 |
| 4,496,210 | 1/1985 | Ansel et al. | 350/96.30 |
| 4,514,037 | 4/1985 | Bishop et al. | 350/96.23 |
| 4,566,437 | 1/1986 | Yamaguchi | 128/4 |
| 4,592,932 | 6/1986 | Biswas et al. | 427/163 |
| 4,597,030 | 6/1986 | Brody et al. | 362/32 |
| 4,611,888 | 9/1986 | Plenovitz et al. | 350/96.26 X |
| 4,613,521 | 9/1986 | Smith, Jr. | 427/169 |
| 4,613,583 | 10/1986 | Tsuno et al. | 350/96.33 |

OTHER PUBLICATIONS

Panoliaskos et al., "Prediction of Optical Fiber Coating Thickness", Applied Optics, vol. 24, No. 15-Aug. 1, 1985, pp. 2309-2312.

Wang et al. "UV-Cured Epoxy-Acrylate Coatings on Optical Fibers. III, Effect of Environment on Long-Term Strength, Bell Laboratories, pp. 1-4.

Vazirani et al., "U.V. Cured Epoxy-Acrylate Coatings on Optical Fibers, I. Chemistry and Application, Bell Laboratories, pp. 1-3.

Gloge, "Optical-Fiber Packaging and Its Influence on Fiber Straightness and Loss", The Bell System Technical Journal, vol., 54, No. 2 Feb., 1975, pp. 245-262.

"Light Wand", Chemical Abstracts, p. 19.

Van-Tec "UDX 70" product literature.

Microvasive "VISICATH" product literature.

FIBER-OPTIC IMAGE-CARRYING DEVICE

This invention relates to fiber-optic image-carrying devices for examining regions that are remote or difficult of access.

Such devices are used in medicine for examining organs, veins and arteries, and other parts of the human body. Similar devices are used in industry, for internal inspection of engines, nuclear reactor tubes and other critical areas.

It is desirable to achieve an image-carrying unit that is very small (e.g., with outside diameter less than 1 mm and preferably about 0.5 mm or less), which is practical to make and which has useful image size, field of view and degree of contrast. It is also desirable to achieve a catheter which combines a flexible image-carrying unit, a means for delivering illumination to the viewing area and a working channel, in an overall assembly that likewise is very small, e.g., less than 3 mm overall diameter.

SUMMARY OF THE INVENTION

According to the invention, an elongated image-carrying member having sufficient flexibility and optical qualities to provide vision for medical catheters, e.g., for small passages and ducts, comprises a multi-fiber micro-unit of diameter of about 0.5 mm, formed of a large multiplicity of glass fibers in coherent array, and a protective polymeric outer portion, the large multiplicity of glass fibers being drawn and fused together over a substantial length and having, as drawn, a glass outer surface, and the protective polymeric outer portion being bonded to the as-drawn outer glass surface of the fused multi-fiber unit over the substantial length.

In preferred embodiments of this and other aspects of the invention, the micro-unit is comprised of the order of two thousand fibers in the coherent array; the outer surface of the micro-unit comprises an encapsulating glass sleeve intimately drawn and fused with the coherent array of fibers; the protective polymeric portion comprises a thermoplastic coating; the member has a characteristic bend radius in the range between about 1 and 6 centimeters, preferably at least at its distal region the bend radius being about 2 centimeters or less; the protective polymeric portion comprises a relatively opaque layer that surrounds the multi-fiber unit, preferably this layer having a thickness of the order of about 0.001 inch and is in a UV-cured state; a transparent layer overlies the relatively opaque layer, the transparent layer having a substantially greater thickness than the relatively opaque layer, and where the transparent layer comprises a substantial thickness of clear material that creates a potential transmission cross-section, the relatively opaque layer, by serving to absorb light that is moving with lateral component toward the multi-fiber unit, prevents the light from being transmitted by wave-guide effect along the transparent layer.

According to another aspect of the invention, such an image-carrying member is incorporated within a flexible catheter which also has an illumination light guide means extending through a lumen of the catheter.

In preferred embodiments of this aspect of the invention, the image-carrying member and the light guide means are contained in separate lumens of the catheter; another lumen provides an open working channel at least as large as the lumen containing the image-carrying member; the catheter has an outer diameter of about 3 mm or less, preferably an outer diameter of the order of 2 mm; the catheter has, at its proximal end, a connector adapted to detachably connect the image-carrying member to a handle which has an associated ocular means and light source means, whereby the catheter can be replaced without replacement of the handle; there is a single distal lens in the form substantially of a sphere disposed at the distal end of the micro-unit, the sphere being of diameter no greater than about 120% of the diameter of the micro-unit, preferably the diameters of the micro-unit and the sphere being of the order of 0.5 millimeter or less; the components provide an improved image attributable to pin-hole optics principles that partially compensate for aberration produced by the spherical lens, preferably the device has a focus distance between about 1 and about 5 to 6 millimeters from the spherical lens over which the device has a magnifying power in reverse relationship to focus distance; the device has a reducing effect at focus distances above about 5 to 6 mm; the device has the ability to produce an image over an arc of at least about 80° in air; and the catheter has an inflatable balloon for placement in the body, a working channel of the catheter providing for flow of fluid to inflate and deflate the balloon.

According to another aspect of te invention, in a remote vision micro-optical device in which a substantially spherical lens of about 0.5 mm diameter delivers an image into an elongated image-carrying member of generally corresponding diameter, the image-carrying member is comprised of a coherent array of a large multiplicity of optical fibers, the coherent array of fibers of the image-carrying member, over at least the majority of its length, comprises, as mentioned above, a drawn and fused micro-unit in which there are of the order of two thousand constituent fibers that are fused to each other, the microunit having a bend radius of 6 centimeters or less.

In preferred embodiments of this aspect of the invention, the lens has a diameter of about 0.020 inch, the diameter of the lens being no greater than about .120% of the diameter of the image-carrying member.

According to another aspect of the invention, a method of examination of small ducts and vessels of a body, including such passages as ureters, eustachian tubes, fallopian tubes, small blood vessels and small passages of the biliary tree, comprises introducing into such a passage the remote vision micro-optical member as described above, and, while moving the micro-optical member axially in the passage, observing the relationship of the change in position of the instrument in the body with respect to the zoomed change of the image of an area of interest along the wall of the small passage.

According to another aspect of the invention, an examination device comprises a hollow metal tube adapted to be inserted into a body, the tube containing and supporting a remote vision micro-optical member as described above, with the lens located in the distal portion of the tube.

According to a further aspect of the invention, a vision system includes the image-carrying micro-optical member described above and a handle to which it is adapted to be connected via a connector, the connector comprising a male member having an accurately machined surface of revolution adapted to interfit with a corresponding female receptacle of the handle, the axis of the micro-unit lying on the axis of the surface of revolution of the connector and the axis of the optics of the handle aligned with the axis of the female receptacle, the end of the male member having a step to one side of the axis adapted to interfit with a step provided within the female receptacle.

In preferred embodiments, two axially spaced apart end surfaces are associated with the step, an interface between the image-carrying micro-unit and a further image-carrying member in the handle being located at one of the end surfaces, and an interface between a light source and a light guide for transmitting illumination to the object to be observed by the lens being located at the other of the spaced apart end surfaces.

According to another aspect of the invention, a connector system is provided for connecting an image-carrying member as described above with a handle having associated optics, comprising a male connector associated with the image-carrying member and having an accurately machined surface of revolution adapted to interfit with a corresponding female receptacle of the handle, the axis of the member lying on the axis of the surface of revolution of the connector and the axis of the optics of the handle aligned with the axis of the female receptacle, the end of the male member having a step to one side of the axis adapted to interfit with a step provided within the female receptacle, a light guide terminating upon the step of the male member and being aligned with a light delivery source within the handle.

According to another aspect of the invention, a flexible fiberoptic probe useful for the examination of small ducts and passages, comprises: an eyepiece, a distal lens means and the remote vision micro-optical member as described above, having of the order of 2,000 coherently arranged fibers, the member extending between the eyepiece and the distal lens means, the distal lens means having a diameter of the order of that of the member and selected to provide a wide angle view in air of about 80° or greater, neutral magnification at a distance selected in the range of 4 to 8 mm and increasing magnification at closer distances down to at least 2 mm.

According to another aspect of the invention, a method of forming the remote vision mico-optical member described above comprises fusing and drawing a multi-fiber micro-unit having about 2,000 clad glass fibers, to form a fused unit having fibers of the order of 8 micron diameter, coating the surface of the micro-unit substantially immediately after drawing with a protective coating, and, during the drawing, maintaining the balance of the physical properties of the glass and the drawing temperature and rate to provide substantially uniform tension throughout the formed micro-unit.

In preferred embodiments, a method for forming the remote vision member in a manner to provide relatively greater flexibility in a distal portion, comprises further drawing the distal portion to smaller diameter; or leaching a limited distal portion to remove at least a portion of the cladding about the fibers.

To summarize particularly salient aspects of the invention, there is provided a multi-fiber micro-unit that may be employed in a micro-optical system to achieve microendoscopy. Due to its flexibility, the unit may be used in flexible as well as rigid imaging-probes. Combined in a micro-optical system with a correspondingly small optical quality spherical lens and closure window, the multi-fiber unit provides a desirable image, with resolution down to about 0.001 inch and an ability to view over an angle of about 80° in air, a distinct advantage in examination of side walls of very narrow passages. The invention also provides a system for detachably connecting the imaging probe containing the micro-optical system with a viewing handpiece containing an ocular system and illumination light source connections that achieves precise alignment of image and illumination components. By this connection system, if the imaging probe is damaged or if it is desirable to restrict use of a probe to a single patient, it becomes practical for the physician simply to replace the relatively inexpensive imaging probe, while continuing to use the handpiece that contains the relatively expensive ocular components.

Other features and advantages of the invention will be understood from the following description of the presently preferred embodiments, and from the claims.

PREFERRED EMBODIMENT

We first briefly describe the drawings:

FIG. 4 shows a needle probe image-carrying inspection device according to the invention while

FIG. 5 shows a flexible catheter inspection device according to the invention, while

FIG. 7 is a side section view of the distal portion of the imaging probe of FIG. 6, while FIG. 7a is an end view taken on line 7a—7a of FIG. 7;

FIG. 8 is an enlarged side section view of the proximal connector of FIG. 6, while FIG. 8a is an end view taken on line 8a—8a of FIG. 8;

FIG. 9 is a side section view of a viewing handpiece for use with the probe of FIG. 6-8;

FIG. 10 is a plan view of the proximal portion of another probe embodiment of the invention, while FIG. 10a is a transverse section view taken on line 10a—10a of FIG. 10;

FIG. 13 is a side section view of the distal end portion of another embodiment of an image-carrying probe member, while

Figure 1:
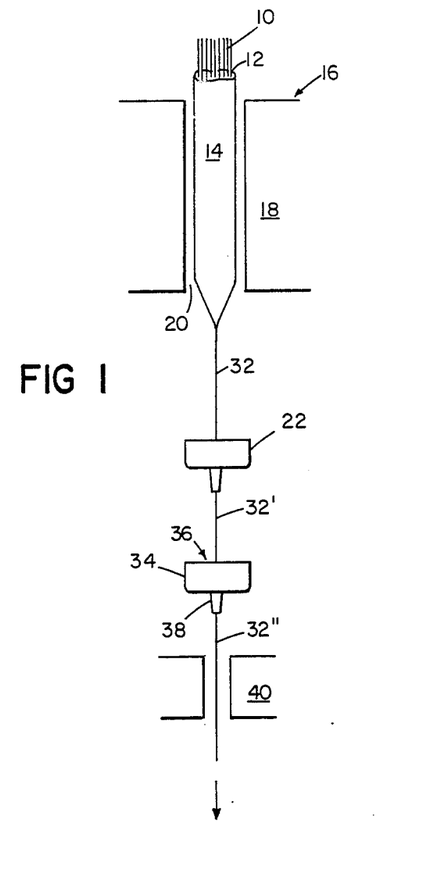
FIG. 1 is a diagrammatic representation of a process for forming an image unit of the invention.

Referring to FIG. 1, a very large number (typically of the order of 2,000, e.g., 1,800) of individual glass optical fibers, each about 0.25 mm or more in diameter and consisting of a core surrounded by a cladding material of relatively lower index of refraction, are assembled in coherent array within a bundle 10 and placed within a glass stuffer tube 12 to comprise preform 14. Tube 12 has an outer diameter of about 40 mm and its material is selected to be at least compatible with and preferably to be the same as the cladding of the individual fibers. In preferred embodiments, the core, cladding and stuffer tube are all of borosilicate glass. By use of glass, especially borosilicate glass, the clad thickness can be quite thin, allowing high packing and hence good contrast resolution to be achieved in the micro-unit being formed. The numerical aperture of glass enables transmission of a wide angle image, which is of particular importance in examining the walls of tiny ducts of the body.

Figure 2:
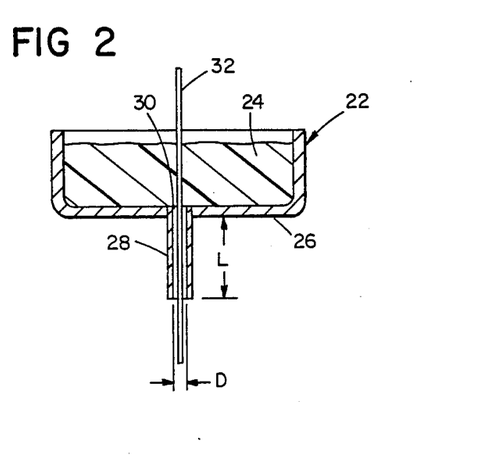
FIG. 2 is an enlarged side section view of a coating cup.

In drawing tower 16, the preform assembly 14 is fed through a heating furnace 18. The preform, including the fibers, is heated to the softening point, in softening zone 20, and is then drawn as a unit to decrease the outer diameter to the desired micro-unit dimension, e.g., to about 0.5 to 1.0 mm (0.020 to 0.040 inch), or less. By maintaining a proper balance between the physical properties of the glass and the drawing temperature and rate, substantially constant tension can be maintained throughout the length of the formed micro-unit, a condition found to be very desirable for achieving a high yield rate of satisfactory units. The drawing action fuses the tiny fibers to one another and fuses the encapsulating layer to the surrounded optical fibers in a uniform way so that the resulting image unit is compact, presents a relatively large active image area for its overall size, and is flexible due to its small bend cross-section. The drawn multi-fiber unit is immediately passed through coating cup 22 containing the relatively opaque coating material 24 that carries an opaque constituent, described in detail below, so that the pristine, as-drawn surface of the glass is immediately protected. Referring also to FIG. 2, the base 26 of the coating cup is in the form of a nozzle 28 defining a narrow aperture 30 of length, L, and diameter, D, selected as described in Panoliaskos, Hallet, and Garis, "Prediction of Optical Fiber Coating Thickness", *Applied Optics*, 24 (15): 2309–2312, Aug., 1985, which is incorporated herein by reference. This cup allows through-passage of the optical fiber bundle and applies a predetermined thickness of coating material 24 about the encapsulating layer, e.g., a thickness between about 0.0005 to 0.002 inch.

In this way, the pristine surface of the drawn unit is immediately protected against moisture, pollutants, etc. in the air to prevent microcracking and the flexibility of the unit is preserved.

If a second, transparent layer of coating material is desired, the relatively opaquely coated optical fiber assembly 32' is directly fed to a second coating cup 34 containing a clear protective coating material 36 of a relative viscosity lower than that of the relatively opaque coating material 24, e.g., to prevent mixing of the material of the two layers. The nozzle 38 of coating cup 34 is also sized and dimensioned for through-passage of the coated fiber assembly 32" with the desired thickness of clear protective coating material, e.g. 0.010 inch.

Figure 1A:
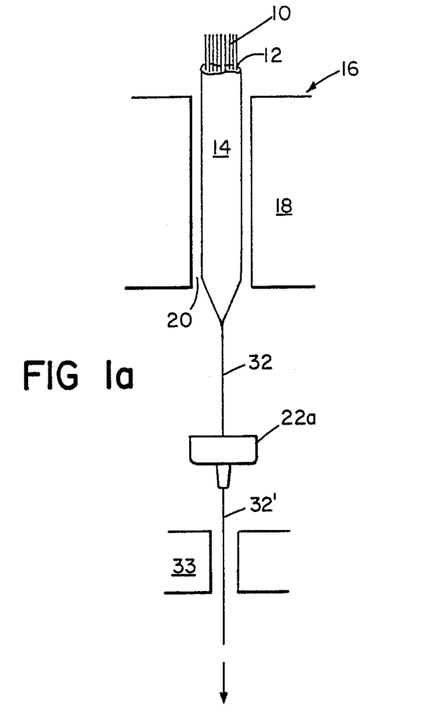
FIG. 1a is a representation of another process for forming an image unit.

Referring to FIG. 1a, a coated optical fiber assembly 32, e.g., for use in a rigid needle probe or where the second transparent layer is not required, is passed through only a single cup 22a to apply the relatively opaque layer.

The coated assembly (32', FIG. 1a; 32", FIG. 1) is then cured by passage through ultraviolet chamber 40.

The U.V. radiation passes into the clear layer (if present) and cures it, while an adequate amount of the radiation continues into the thin relatively opaque coating and cures it. Thus there is formed a solid, nonsticking coating about the fused micro-unit, this coating permitting handling of the unit during manufacture and serving to protect the unit from damage during use.

In the preferred embodiment, the relatively opaque coating material is formulated to provide a thin layer containing sufficient black pigment to substantially absorb light moving laterally. The preferred coating material includes a photo-initiator for UV curing, and the level of pigment particles in the coating layer is controlled to permit sufficient penetration of UV energy into the coating layer for complete curing.

One particular coating formulation found acceptable in thicknesses between about 0.0005 and 0.002 inch is as follows:

(a) an acrylated urethane oligomer;
(b) a reactive diluent, e.g. N-vinylpyrrolidone, employed to reduced viscosity of the urethane and improve flexibility;
(c) a photoinitiator, e.g. a commercial blend of benzophenone and 1-hydroxycyclohexyl phenyl ketone; and
(d) a carbon pigment dispersion in monomer.

In the preferred formula, component (a) is about 80 to 85 percent of the mixture, component (b) is about 10 to 15 percent, component (c) is provided in sufficient quantity to perform its initiation function, being dependent upon the intensity of the radiation and speed of draw of the fibers, typically a quantity about 1 percent, and component (d) is about 1 to 2 percent. (All percentages refer to weight.)

The clear coating, if applied, may comprise the same components, omitting the carbon pigment.

Figure 3:
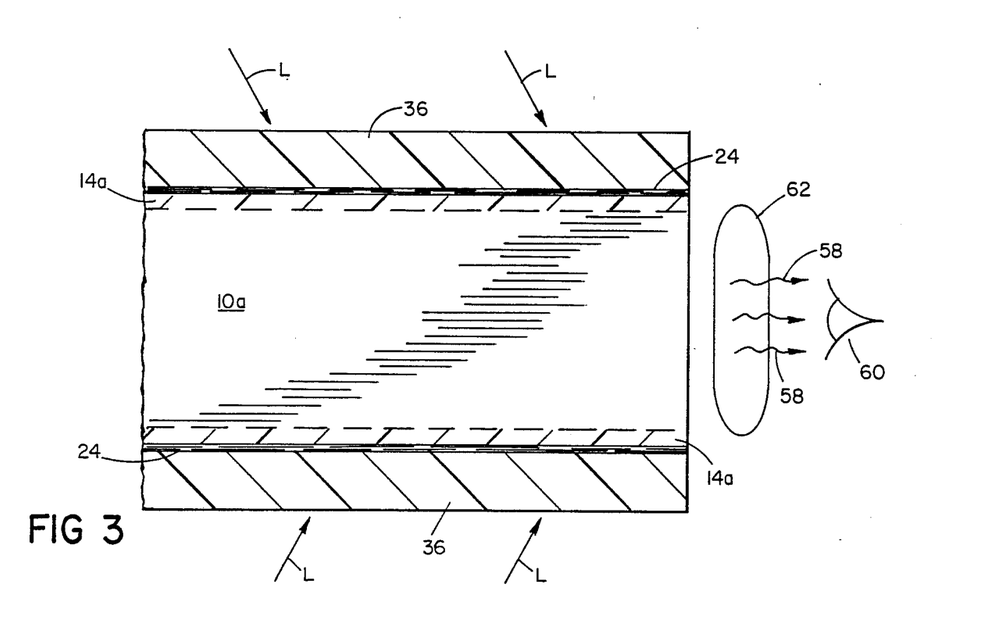
FIG. 3 is a longitudinal cross-section of a fused fiber-optic unit made according to the invention.

Referring to FIG. 3, without the relatively opaque coating 24 of the invention, a certain portion (indicated by arrows L) of light traveling, e.g., through an illumination means would escape laterally and infiltrate clear coating 36, if present, and clear encapsulating layer 14a. Due to the differing refractive indices of the adjacent layers, the encapsulating layer 14a, and the clear coating 36, would act in the manner of wave-guides for rays having a longitudinal component, thus conducting unwanted light toward the viewer, and presenting distracting halos of light 62 about the image. Also, some of the light in layer 14a might enter the fibers 10a themselves, resulting in a "flare" condition in the image 58 delivered to the viewer 60, i.e., washing out or bleaching of the image, with loss of contrast Such undesirable wave-guiding effects are minimized according to the invention while preserving the desired small size of the fiber unit. "Wave guiding" occurs by repeated reflection of light as it progresses down a guide, but because of the thin, relatively opaque coating of the invention, absorption of some light occurs each time a ray in one of the clear layers strikes the respective interface with the relatively opaque layer, thus rapidly decreasing the energy of the ray. In this manner, even though light enters the clear layers, substantial longitudinal transmission of the light can be defeated.

A micro-optical system for viewing in remote areas, e.g., of the body, is formed by first assembling a coherent bundle of about 1,800 borosilicate glass monofibers (0.026 inch outer diameter, 0.022 inch core) in a borosilicate glass stuffer tube, drawing the assembly and coating the pristine surface of the unit with the relatively opaque coating only, as described above. The resulting drawn, fused, image unit has an overall diameter of about 0.020 inch (0.016 inch central active fiber diameter, with each fiber about 8 micron diameter, 0.00075 inch stuffer tube drawn thickness, and about 0.0015 inch relatively opaque, U.V. cured coating thickness) and has a bend radius in the range of about 1 to 6 cms, preferably about 2 cms or less.

Figures 7, 7A, 8, 8A:
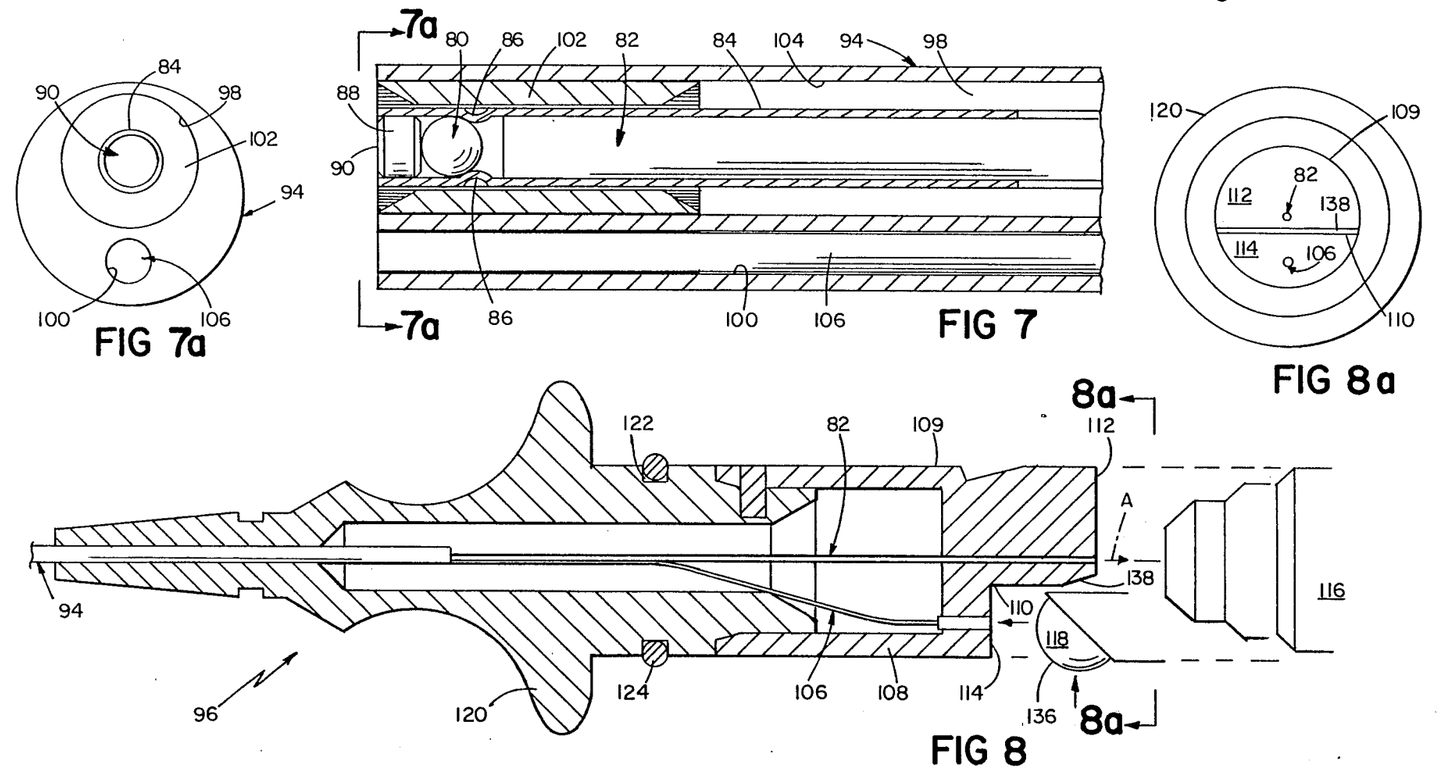

Referring to FIG. 7, a tiny, substantially spherical lens of optical quality, e.g., glass, sapphire, or other suitable optical material is selected to have a diameter close to (no greater than about 120% of) the diameter of the multi-fiber unit of bundle 82. A short, rigid, metal tube 84, about 2 to 3 mm long with an inner diameter of 0.020 inch, is provided with indentations at a predetermined lens-locating position along the length of the tube. The tiny lens is inserted into the distal end of this small tube, is advanced proximally until it rests against the indentations, and is then secured, e.g., with epoxy adhesive. A circular window 88, e.g., glass, sapphire, or other suitable optical material, is inserted into the distal end of the tube to butt against the lens, and is secured in place with epoxy adhesive. The distal end of the tube is then ground flush with the distal surface 90 of the window.

The distal end of the coated, coherent multi-fiber bundle 82 is inserted into the proximal end of the tube 84 and advanced until it butts against the indentations 86. Preferably, at that point, for optimizing the carried image, the assembly person, while viewing through the system, moves the distal end surface of the multi-fiber bundle away from engagement with the indentations until the optimal image is obtained. Unit 82 is then secured to the tube by epoxy adhesive. (By selection of materials, properties and the configuration of the elements, this optimizing step can, in some instances, be omitted, and the multi-fiber bundle secured to the tube in butting engagement with the lens.)

Figure 4:
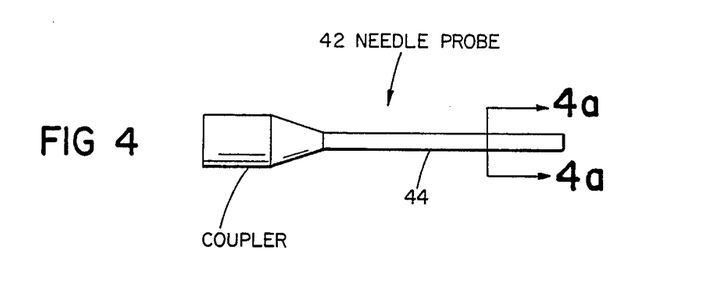
Figure 4A:
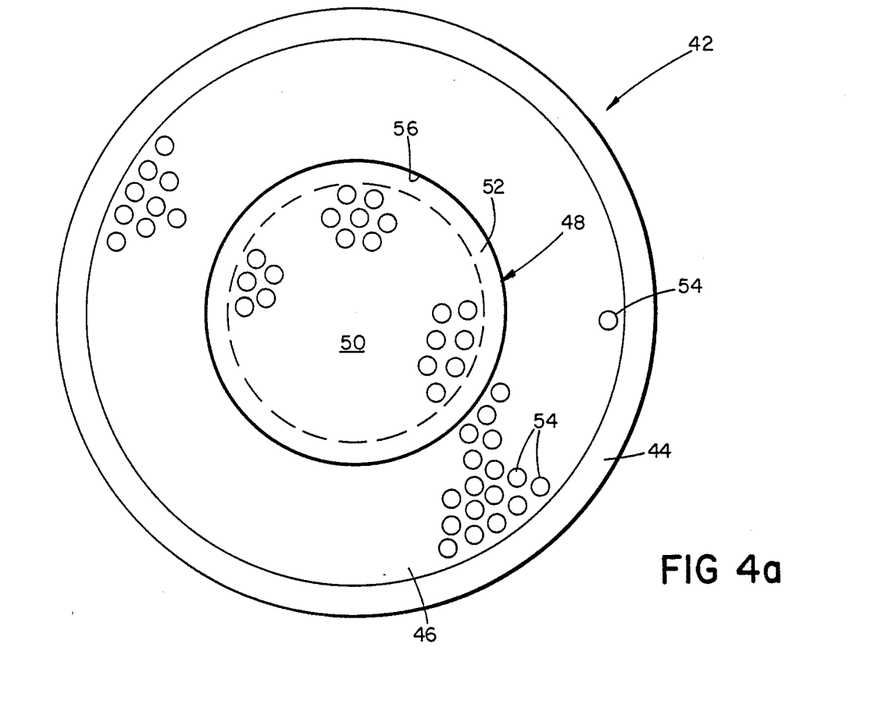
FIG. 4a is a much enlarged end view thereof.

Referring now to FIGS. 4 and 4a, rigid needle probe inspection device 42, formed according to the invention, may employ the lens system of FIG. 7. This rigid probe consists of a stainless steel hypodermic tube 44, e.g., 20.0 cm long and about 1.0 mm diameter with a wall thickness of 0.002 inch, or up to 2.0 mm diameter with a wall thickness of 0.005 inch, an illuminaion means 46, an image-carrying optical fiber bundle 48, formed as above, having an inner core 50 of optical fibers (only a few are shown by way of example) surrounded by encapsulating layer 52, the material of the drawn stuffer tube 12 of FIG. 1. The illumination means is a circumferential, fixed array of illumination-carrying optical fibers 54 (again only a few are shown) lying closely about the image-carrying bundle, within the hypodermic tube. About the peripheral surface of the fused image unit, between the light-carrying illumination fibers and the image-carrying fibers, is disposed the thin, e.g., of the order of about 0.0005 to 0.002 inch, layer of polymeric, relatively opaque material 56 of the invention. This layer prevents wave guiding according to the explanation above.

Figure 5:
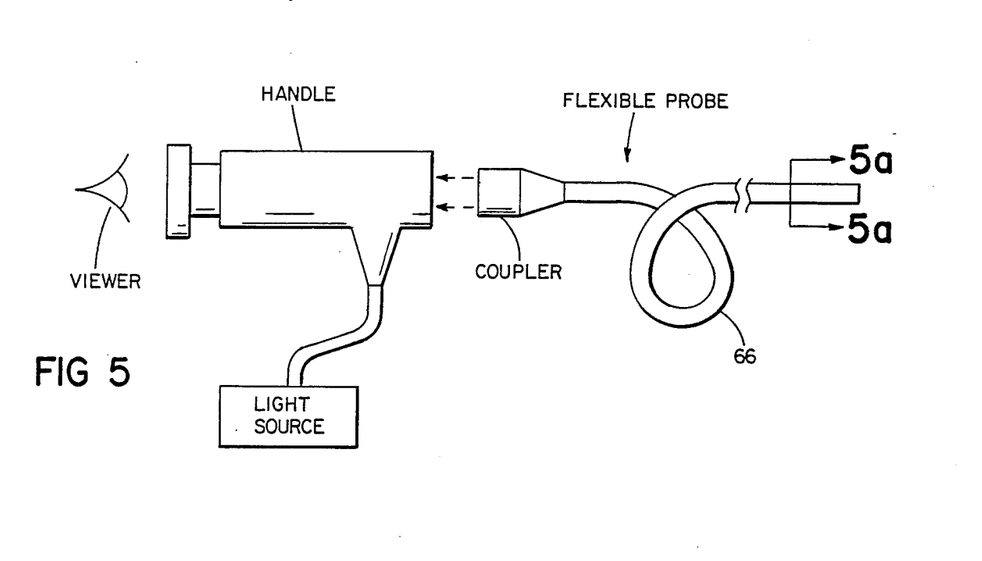
Figure 5A:
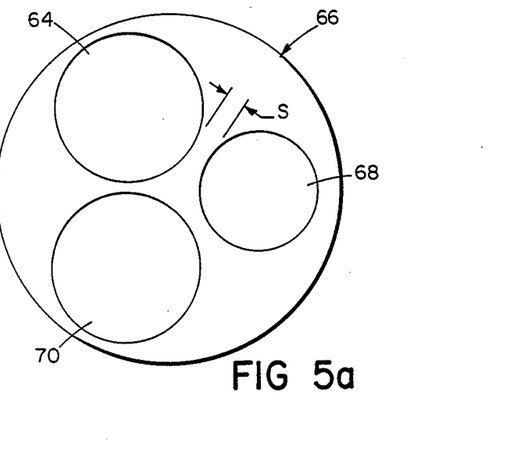
FIG. 5a is an end view of the catheter and FIG. 5b is a much enlarged sectional view of a portion of FIG. 5a containing its fused image unit.
Figure 5B:
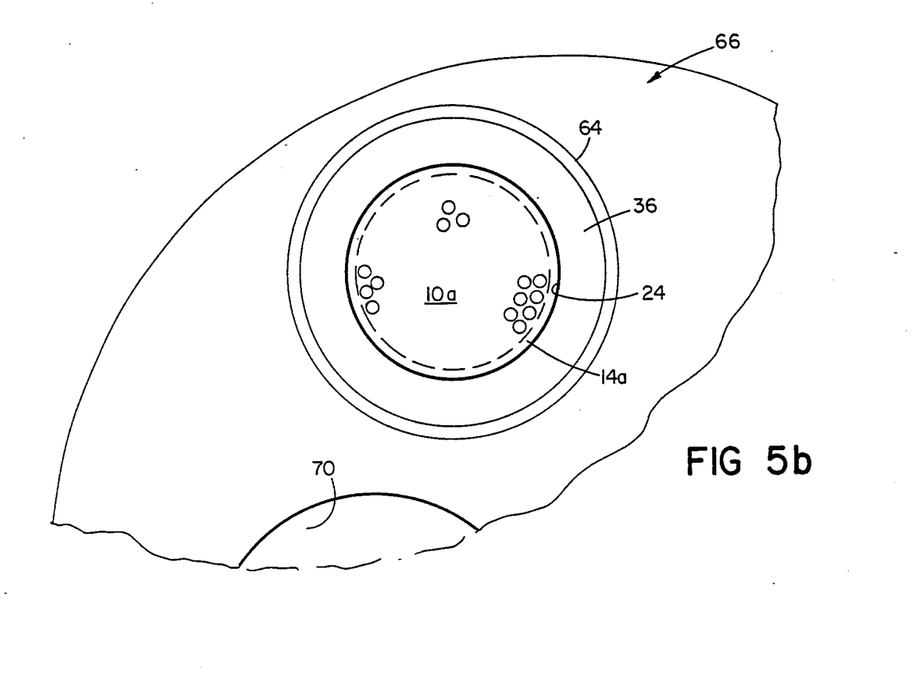

Referring to FIGS. 5, 5a and 5b, a viewing catheter is shown, which may employ the lens system of FIG. 7. This catheter comprises semiflexible fused bundle 64, having a bending radius, e.g., of about 1 to 2 centimeters, placed within a lumen of a flexible, polymeric multilumen catheter 66, e.g., 130 cm long and 2.0 mm diameter, as shown in FIGS. 5a and 5b, with illumination provided by monofilament 68 in a second lumen.

The third lumen provides an open working channel 70. Without protection of the relatively opaque coating of the invention, the separation, S, in the catheter between the image-carrying lumen and the illumination-carrying lumen is so small as to allow infiltration of light from the illumination means to the fused image unit and reduction of image quality as described above. Referring to FIG. 5b, the relatively opaque coating 24 of the invention is disposed between the inner clear encapsulating layer 14a and the outer clear protective coating 36 provided for protection of the bundle. As described above, the relatively opaque layer attenuates infiltrating light and prevents the inner layer from acting in the manner of a wave-guide, serving to provide a better image to the viewer.

The fused bundle (in comparison to so-called leached bundles) has a larger active image area for a comparably sized unit, i.e., less space between fibers, and in a space-saving way achieves necessary strength.

Figure 6:
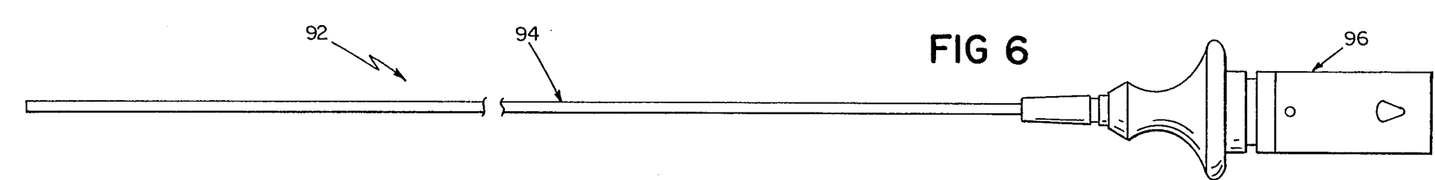
FIG. 6 is a side view of one embodiment of an elongated imaging probe of the invention with the thickness of the probe exaggerated in size for purpose of illustration.

Referring now to FIGS. 6–8, an imaging probe is shown. It comprises a flexible catheter 92 consisting of a flexible distal sheath 94 of predetermined length, e.g., up to about 100 cms, and a proximal connector 96. The sheath, in the embodiment shown, defines a pair of lumens 98, 100, shown in FIGS. 7 and 8. The first and larger lumen 98 contains the elongated, image-carrying micro-optical system, including multi-fiber bundle 82 terminating distally in tube 84 which also contains spherical lens 80, and closure window 88, assembled as described above. The distal end of the tube 84 extends through and is secured within sleeve 102 (plastic or metal), which fills the annular cavity between the tube 84 and the wall 104 of the lumen to seal the end of the lumen against infiltration of fluid. The second, smaller lumen 100 contains a light guide 106, e.g., consisting of one or more fibers, for providing illumination for viewing at the distal tip.

Referring to FIGS. 8 and 8a, the image-carrying bundle 82 and illumination light guide 106 extend proximally into male connector 96. The connector has a cylindrical body 108 with a proximal end portion having a surface of revolution 109 precisely machined for close-fit within the receiving aperture of a viewing handpiece (FIGS. 5 and 9), and includes an end step 110 spaced from the axis of the surface of revolution to match with a like step in the aperture to facilitate proper rotational alignment of the connector within the hand piece. The proximal end of image-carrying bundle 82 terminates at the major surface 112, e.g., encompassing about 200° of revolution of the proximal end of the connector, in alignment with the connector axis, A, while the illumination light guide 106 terminates on the more distal, minor surface 114. By providing a close tolerance fit between the stepped connector surfaces and the corresponding surfaces of the hand piece, precise alignment of the end face of the image-carrying bundle 82 with the ocular system 116 in the handpiece and alignment of the end face of the illumination member 106 with the path of illuminating light from the light source 118 is ensured. The stepped displacement of the connector image surface 112 and illumination surface 114 from each other also reduces the possibility of contamination of the image from the bundle 82 by errant illumination light directed toward the light guide 106. The body of the connector has a radial flange 120 to aid the operator in rotation and insertion, and also removal, of the connector. The body also defines a circumferential groove 122 for receiving an O-ring 124, which provides a liquid-tight seal when the connector is assembled with the handpiece.

Figures 9, 10, 10A:
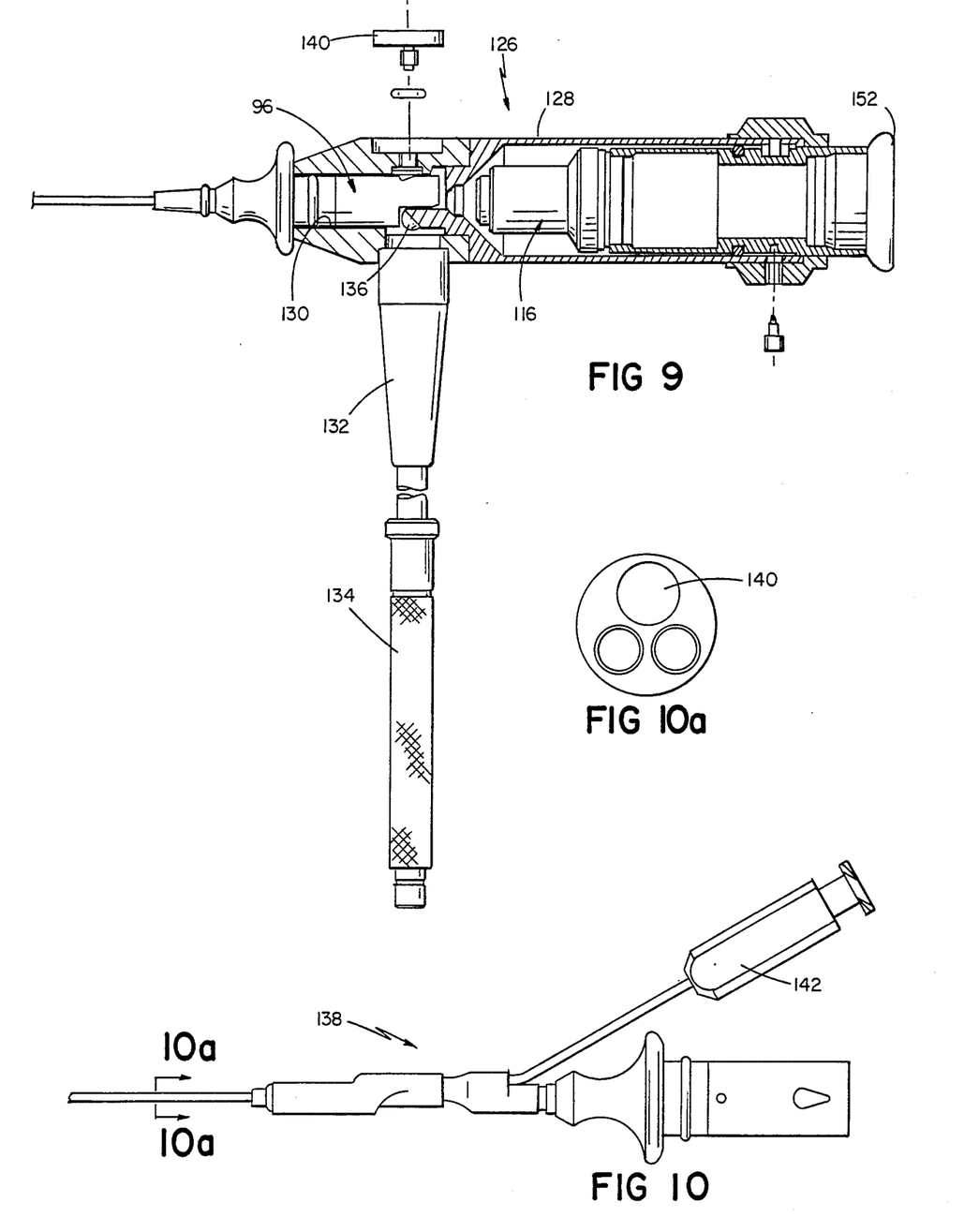

The fiberoptic viewing handpiece 126, seen diagramatically in FIG. 5 and in section in more detail in FIG. 9, consists of a body 128 defining a distal connector-receiving aperture 130 and containing ocular system 116 for viewing through the image-carrying micro-optical system. Extending below the handpiece body is a handle 132, which terminates in a connection to an illumination light carrying cable 134 from a light source (not shown). Light from the source is directed into reflector 136, a half sphere, silvered on the planar reflective surfaces and on the spherical surface except for two appropriate apertures, the reflective surfaces acting as stray light traps. The proximal connector 96 of the imaging probe 92 is inserted into aperture 130 with close fit, the step-form of the connector requiring proper rotational orientation, facilitated by beveled surface 138, before full insertion is achieved. Once inserted, the connector is secured by tightening knob 140.

Other embodiments of the invention are within the claims. For example, to further reduce the overall diameter of the device, the diameter of the encapsulating layer may be reduced by eliminating the stuffer tube and assembling the fiber bundle by other means, e.g., by use of a glass frit bonding material at least compatible with the cladding material of the individual fibers, the frit forming a relatively thinner encapsulating layer during the drawing step. Also, a relatively opaque coating may be cured thermally or catalytically, or by use of an infrared heater, although in the semiflexible, dual-coated optical fiber bundle shown, this would occur before application of the second, clear protective coating, which would then typically be cured by exposure to UV radiation.

Figures 11, 12:
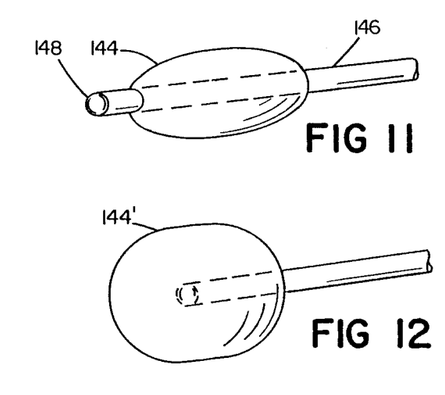
FIGS. 11 and 12 are somewhat diagrammatic side views of other embodiments of the distal ends of imaging probes of the invention.
Figure 13:
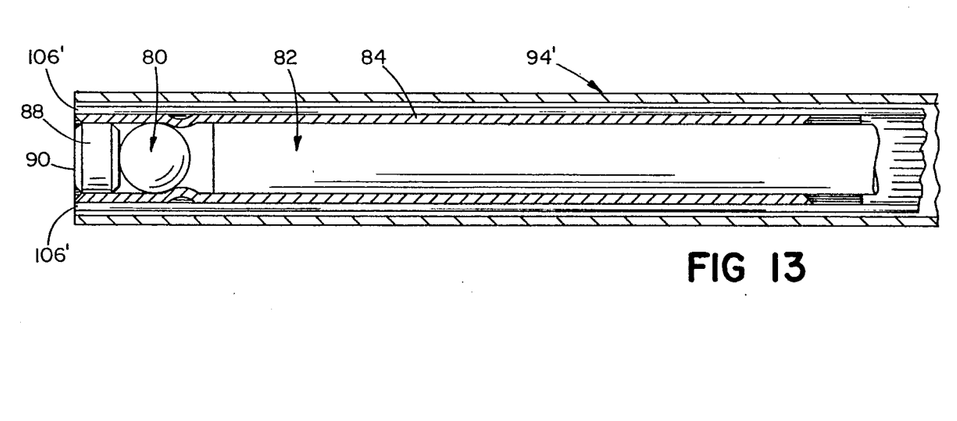
Figure 14:
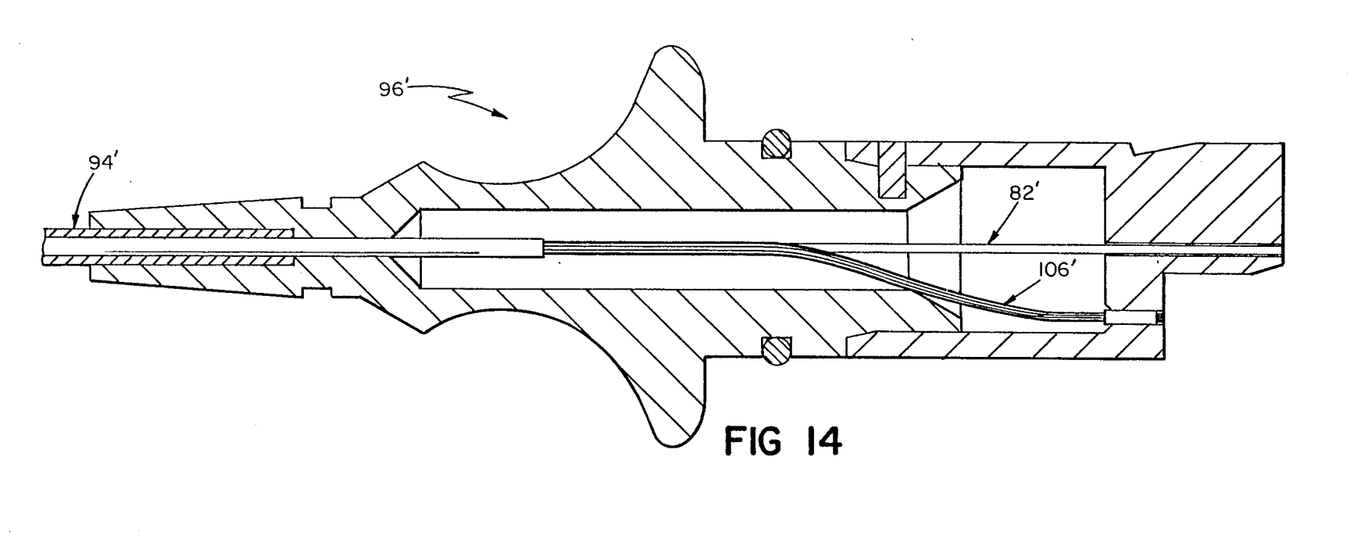
FIG. 14 is a similar view of the proximal connector theref.

The sheath may define more than one open working channel, e.g., for introduction of fluid for flushing or irrigating or for dilatation of the duct surrounding the distal end of the probe for increased field of view, or for use of a guidewire or other instruments such as retrieval baskets or forceps. Referring to FIGS. 10 and 10a, an imaging probe 138 has a single working channel 140, terminating proximally in leur connection 142. The working channel may also be employed for flow of fluid for inflation and deflation of a balloon 144 adjacent the distal end of the catheter 146, e.g., proximal of the viewing lens 148 (FIG. 11), or about the tip, with the image received through the balloon 144' (FIG. 12). Also, referring to FIGS. 13 and 14, the illumination light guide 106' may be in the form of a plurality of fibers which are disposed about the image-carrying bundle 82 within the connector 96' and extend within the catheter sheath 94', alongside the bundle, as shown in FIG. 4a, and the distal tube 84, to terminate distally in a halo-like array about the image-receiving closure window surface 90.

Figure 15:
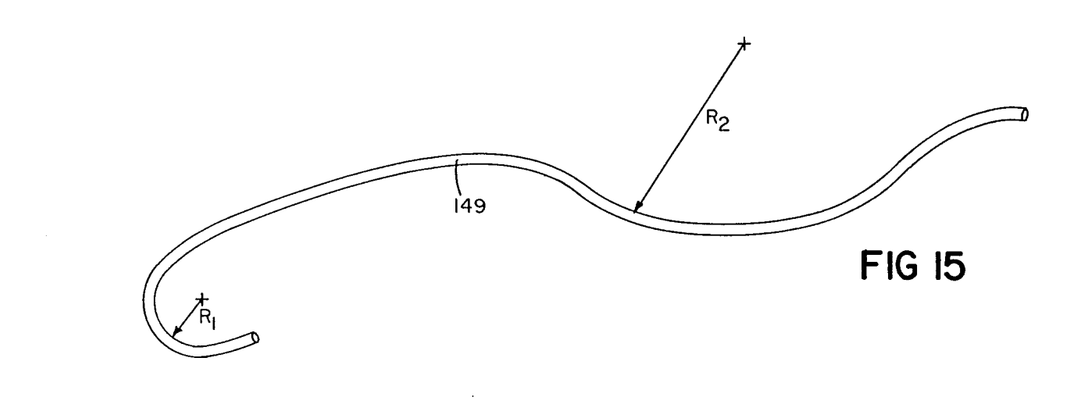
FIG. 15 is a diagrammatic view of an embodiment of the probe of the invention having varying flexibility, with a highly flexible distal end.
Figure 16:
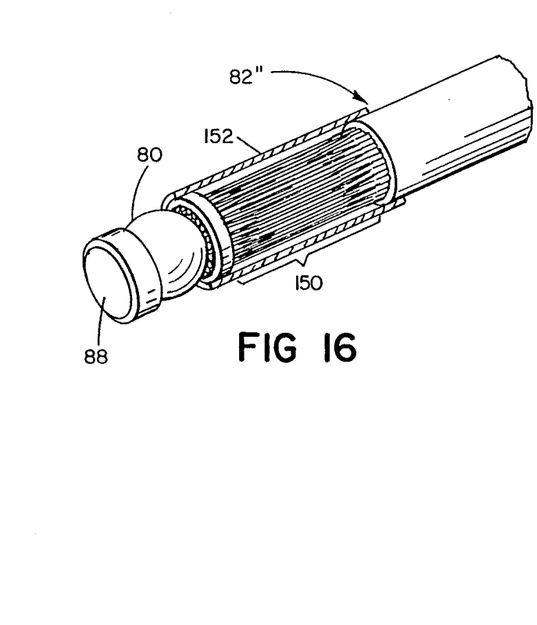
FIGS. 16 and 17 are somewhat diagrammatic side views of the distal end portion of embodiments of image units that enable the realization of the image-carrying member of FIG. 15.
Figure 17:
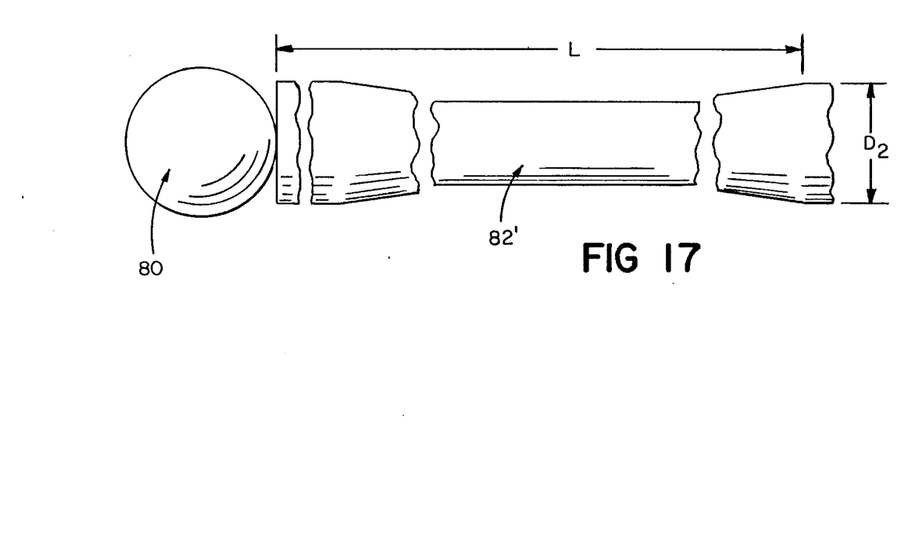

Referring to FIGS. 15, 16 and 17, a catheter with increased flexibility at the distal tip region is shown, e.g., to provide a tip bend radius, $R_1$, e.g., of the order of about 2 cms or less, as compared to a larger bend radius, $R_2$, of the body of the probe 149. The more flexible distal end serves to facilitate negotiation of small radius bends in passages of the body, e.g., a 90° turn into the coronary artery. For this purpose, in FIG. 16, the fused bundle 82" is comprised of a leachable (or water soluble) stuffer tube and the fibers include a similarly leachable second clad, known as a super cladding. The drawn and fused unit may be selectively leached over a limited distal length as shown in the figure to remove the leachable stuffer tube and a leachable super cladding on individual fibers over a length, L, e.g., of about 5 to 10 cms. The exposed, pristine, separated individual fibers are then lubricated, e.g., with carbowax, silicone oil or the like, and encased within a jacket 152. In FIG. 17, the fused bundle 82' may be selectively drawn down to a smaller diameter, $D_1$, e.g., 75 to 85% of the original diameter, $D_2$, over a length, L, e.g., 5 to 10 cms. The outer surface of the reduced diameter segment may be immediately recoated in the manner described above, or the coating may be sufficiently flexible to be drawn with the bundle, without need for recoating. Alternatively, a fused bundle may be selectively treated, e.g., by tempering, to achieve segments of relatively greater flexibility.

Where desired, the micro-optical viewing system of the invention enables introducing the distal end of the imaging probe into the body percutaneously, i.e., via a small puncture opening, and advancing the probe tip while viewing via the eyepiece. The flexible imaging probe has particular application to examination of small diameter ducts and passages of the body, e.g., the ureter (2 mm diameter typical), the biliary tree (4 mm), eustachian tubes (2 mm or less), the Fallopian tubes (1.5 to 2 mm) and blood vessels, e.g., the coronary arteries (2 to 4 mm diameter typical). The overall diameter of the imaging probe containing the micro-optical viewing system, its length and the provision and size of its open lumens is dependent upon the procedure to be performed. By way of example only, the following characteristics may be employed:

| Description | Overall Diameter (mm) | Length (cm) | Open Lumens Number | Open Lumens Diameter(s) |
| --- | --- | --- | --- | --- |
| ureteral visual catheter | 2.8 | 60 | 2 | .018 inch .042 inch |
| direct visual lavage of pulmonary system | 4.3 | 60 | 1 | 2.6 mm |
| endotracheal tube visual catheter | 2.2 | 60-Adult 40-pediatric | — | .042 inch |
| biliary catheter | 2.0 | 60 | 2 | .010 inch .038 inch |
| angioscope | 1.2 | 100 | — | — |
| eustachian tube visual catheter | 1.2 | 23 | — | — |

Rigid embodiments of the imaging probe may also be used percutaneously, e.g., for visual examination of the liver, biliary tree, pancreatic duct and short vessels, and also for examination of joints and the spine.

By selection of the components of the micro-optical system, i.e., the multi-fiber fused bundle, along the lines mentioned above, and the optical quality of the spherical lens and closure window, there is provided a viewing system particularly suited for medical examination.

To examine a point in the body employing the imaging probe of the invention, the physician introduces the distal tip of the imaging probe into the body and, while viewing through the eyepiece (152, FIG. 9), moves the distal tip toward and away from the point he wishes to examine, observing the relationship of the distance of movement of the probe in the body with respect to the change of the viewed image. In the preferred embodiment described, objects viewed at a range of about 4 to 8 mm, and preferably about 5 to 6 mm, from the distal surface 90 are seen at about actual size, while objects seen from about 5 to 6 mm down to about 1 mm are seen with increasing magnification, the closer the distance, and objects beyond about 5 to 6 mm (to infinity theoretically, although the practical maximum range in the body is about 15 to 20 mm) are seen with decreasing size, the longer the distance. The result during movement of the catheter is a zoomed effect, with a much improved image, likened to taking a zoom microscope into the body, that provides resolution down to about 0.001 inch. Thus the invention includes the realization that distortion of such a lens, rather than a detriment, can be used in a highly constructive way.

The relatively high quality of the image achieved may be attributable to a kind of field flattening effect caused by the pin hole principle, due to the small size of the micro-unit. Also, the spherical aberration of the created image, attributable to the spherical lens 80, provides an added advantage in examining the walls of small passages, in which it would not be possible to obtain a head-on inspection. The side view of the passage wall is presented to the eye as a somewhat expanded, and flattened image, a format that is convienent to examine, with appearance somewhat resembling the mercator projection used in map making.

In the case of the wall of a narrow passage, the wide angle optical system has the effect of bending the magnified position of the tube wall toward the viewer to enable a detailed examination despite the end on relationship of the probe to the passage. By slight adjustment of position, the operator may shift from microscopic to actual scale view of the same area, and thus in real time may assemble a great deal of meaningful optical information concerning a region of interest within the body.

Finally we mention that certain principles of the invention related to the coated multi-fiber micro-unit per se can be applied to noncoherent light-transmitting fused fiber bundles with benefit in appropriate circumstances.

What is claimed is:

1. A remote vision micro-optical device in which a lens system of a diameter of about 0.020 inch and comprising at least two substantially spherical lens surfaces is adapted to deliver an image into an elongated image-carrying member of generally corresponding diameter, the image-carrying member comprised of a coherent array of a large multiplicity of optical fibers, the diameter of said lens system being no greater than about 120% of the diameter of said image-carrying member, and said coherent array of fibers comprising over at least the majority of its length, a drawn and fused micro-unit in which there are of the order of two thousand constituent fibers that are fused to each other, said microunit having a bend radius of 6 centimeters or less.

2. A remote vision micro-optical device in which a lens system of about 0.5 mm diameter and comprising at least two substantially spherical lens surfaces is adapted to deliver an image into an elongated image-carrying member of generally corresponding diameter, the image-carrying member comprised of a coherent array of a large multiplicity of optical fibers, wherein said coherent array of fibers comprises, over at least the majority of its length, a drawn and fused micro-unit in which there are of the order of two thousand constituent fibers that are fused to each other, said microunit having a bend radius of 6 centimeters or less, and said drawn, fused, multi-fiber micro-unit comprises glass fibers and has a glass outer surface, and a polymeric protective outer portion is bonded to the pristine as drawn outer glass surface of said micro-unit.

3. A catheter comprising a sheath defining at least a first lumen and a second lumen,
   said first lumen containing a remote vision micro-optical device in which a lens system of a diameter of about 0.020 inch and comprising at least two substantially spherical lens surfaces is adapted to deliver an image into an elongated image-carrying member of generally corresponding diameter, the image-carrying member comprised of a coherent array of a large multiplicity of optical fibers, the diameter of said lens system being no greater than about 120% of the diameter of said image-carrying member, and said coherent array of fibers comprising over at least the majority of its length, a drawn and fused micro-unit in which there are of the order of two thousand constituent fibers that are fused to each other, said microunit having a bend radius of 6 centimeters or less, and
   said second lumen defining a working channel for introduction of fluid into a patient's body.

4. A catheter comprising a sheath defining at least a first lumen and a second lumen,
   said first lumen containing a remote vision micro-optical device in which a lens system of about 0.5 mm diameter and comprising at least two substantially spherical lens surfaces is adapted to deliver an image into an elongated image-carrying member of generally corresponding diameter, the image-carrying member comprised of a coherent array of a large multiplicity of optical fibers, wherein said coherent array of fibers comprises, over at least the majority of its length, a drawn and fused micro-unit in which there are of the order of two thousand constituent fibers that are fused to each other, said microunit having a bend radius of 6 centimeters or less, and said drawn, fused, multi-fiber micro-unit comprises glass fibers and has a glass outer surface, and a polymeric protective outer portion is bonded to the pristine as drawn outer glass surface of said micro-unit, and
   said second lumen defining a working channel for introduction of fluid into a patient's body.

5. An examination device comprising a hollow metal tube adapted to be inserted into a body, said tube containing and supporting a remote vision micro-optical device in which a lens system of a diameter of about 0.020 inch and comprising at least two substantially spherical lens surfaces is adapted to deliver an image into an elongated image-carrying member of generally corresponding diameter, the image-carrying member comprised of a coherent array of a large multiplicity of optical fibers, the diameter of said lens system being no greater than about 120% of the diameter of said image-carrying member, and said coherent array of fibers comprising over at least the majority of its length, a drawn and fused micro-unit in which there are of the order of two thousand constituent fibers that are fused to each other, said microunit having a bend radius of 6 centimeters or less,
   said lens system located in a distal portion of said tube.

6. An examination device comprising a hollow metal tube adapted to be inserted into a body, said tube containing and supporting a remote vision micro-optical device in which a lens system of about 0.5 mm diameter and comprising at least two substantially spherical lens surfaces is adapted to deliver an image into an elongated image-carrying member of generally corresponding diameter, the image-carrying member comprised of a coherent array of a large multiplicity of optical fibers, wherein said coherent array of fibers comprises, over at least the majority of its length, a drawn and fused micro-unit in which there are of the order of two thousand constituent fibers that are fused to each other, said micro­unit having a bend radius of 6 centimeters or less, said lens system located in a distal portion of said tube.

7. A vision system including a remote vision micro-optical device in which a lens system of about 0.5 mm diameter and comprising at least two substantially spherical lens surface is adapted to deliver an image into an elongated image-carrying member of generally corresponding diameter, the image-carrying member comprised of a coherent array of a large multiplicity of optical fibers, and said coherent array of fibers comprises over at least the majority of its length, a drawn and fused micro-unit in which there are of the order of two thousand constituent fibers that are fused to each other, said microunit having a bend radius of 6 centimeters or less, and a handle to which said micro-optical device is adapted to be connected via connector, said connector comprising a male member having a machined surface of revolution adapted to closely interfit with a corresponding female receptacle of said handle, the axis of said multi-fiber micro-unit lying on the axis of said surface of revolution of said male member and the axis of optics of said handle aligned with the axis of said female receptacle, the end of said male member having a step to one side of said axis adapted to interfit with a step provided within said female receptacle.

8. The vision system of claim 7 wherein two axially spaced apart end surfaces are associated with said step, an interface between said image-carrying micro-unit and a further image-carrying member in said handle being located at one of said end surfaces, and an interface between a light source and a light guide for transmitting illumination to the object to be observed by said lens being located at the other of said spaced apart end surfaces.

9. A connector system for connecting an image-carrying multi-fiber member with a handle and associated optics means for transmission of an image from said image-carrying multi-fiber member, said connector system comprising a male connector associated with said image-carrying member and having an accurately machined surface of revolution adapted to interfit with a corresponding female receptacle of said handle, the axis of said multi-fiber member lying on the axis of said surface of revolution of said male connector and the axis of the optics means of said handle aligned with the axis of said female receptacle, the end of said male connector having a step to one side of said axis adapted to interfit with a step provided within said female receptacle, a light guide terminating upon said step of said male connector and being aligned with a light delivery source within said handle.

10. A flexible fiberoptic probe useful for the examination of small ducts and passages, comprising: an eyepiece, a distal lens means and a flexible, image-conducting, drawn and fused multi-fiber micro-unit less than 0.5 mm in diameter and having of the order of 2,000 fibers, said multi-fiber micro-unit extending between said eyepiece and said distal lens means and adapted to transmit an image between said distal lens means and said eyepiece, said distal lens means having a diameter of the order of that of said multi-fiber unit, and said distal lens means having a viewing angle in air of greater than 80°, and said distal lens means having neutral magnification at a range of 4 to 8 mm, and said distal lens means having increasing magnification at distances from about 4 mm down to at least 2 mm.

11. A method of examination of small ducts and vessels of a body, including such passages as ureters, eustachian tubes, fallopian tubes, small blood vessels and small passages of the biliary tree, said method comprising introducing into a said passage a remote vision micro-optical device in which a lens system of a diameter of about 0.020 inch and comprising at least two substantially spherical lens surfaces is adapted to deliver an image into an elongated image-carrying member of generally corresponding diameter, the image-carrying member comprised of a coherent array of a large multiplicity of optical fibers, the diameter of said lens system being no greater than about 120% of the diameter of said image-carrying member, and said coherent array of fibers comprising over at least the majority of its length, a drawn and fused micro-unit in which there are of the order of two thousand constituent fibers that are fused to each other, said microunit having a bend radius of 6 centimeters or less, observing, via said remote vision micro-optical device, an image of an area of interest within said passage, and, while moving said micro-optical device axially in said passage, observing the relationship of change in position of said device in the body with respect to change of said image of said area of interest.

12. A method of examination of small ducts and vessels of a body, including such passages as ureters, eustachian tubes, fallopian tubes, small blood vessels and small passages of the biliary tree, said method comprising introducing into a said passage a remote vision micro-optical device in which a lens system of about 0.5 mm diameter and comprising at least two substantially spherical lens surfaces is adapted to deliver an image into an elongated image-carrying member of generally corresponding diameter, the image-carrying member comprised of a coherent array of a large multiplicity of optical fibers, wherein said coherent array of fibers comprises, over at least the majority of its length, a drawn fused micro-unit in which there are of the order of two thousand constitutent fibers that are fused to each other, said microunit having a bend radius of 6 centimeters or less, observing, via said remote vision micro-optical device, an image of an area of interest within said passage, and, while moving said micro-optical device axially in said passage, observing the relationship of change in position of said device in the body with respect to change of said image of said area of interest.

13. The method of claim 11 or 12 comprising the further steps of providing a catheter defining at least a first lumen and a second lumen, said second lumen defining a working channel for introduction of fluid into the body, and disposing said remote vision micro-optical device within said first lumen of said catheter for introduction of said device within said catheter first lumen into the body.

* * * * *

UNITED STATES PATENT AND TRADEMARK OFFICE
CERTIFICATE OF CORRECTION

PATENT NO. : 4,772,093
DATED : September 20, 1988
INVENTOR(S) : John E. Abele, et al.

It is certified that error appears in the above-identified patent and that said Letters Patent is hereby corrected as shown below:

Under U.S. PATENT DOCUMENTS, page 2, 2nd column, 3rd U.S. reference from the bottom, "Plenovitz" should be --Prenovitz--;

Col. 2, lines 13-15, delete "pin-hole optics principles that partially compensate for aberration produced by the spherical lens," and insert --the small size of the micro-unit and use of a spherical lens in head-on inspection of a passage, to examine the sidewalls,--;

Col. 2, line 25, "te" should be --the--;

Col. 5, line 7, delete "borosilicate";

Col. 6, line 65, delete "borosilicate";

Col. 7, line 45, "illuminaion" should be --illumination--;

Col. 9, line 13, "surfaces" should be --surface--;

Col. 9, line 43, "leur" should be --luer--;

Col. 11, lines 13-14, delete "a kind of field flattening effect caused by the pin hole principle, due to";

Col. 11, lines 18-19, delete "in which it would not be possible to obtain" and insert --with--.

Signed and Sealed this

Twenty-eighth Day of March, 1989

Attest:

DONALD J. QUIGG

*Attesting Officer*     *Commissioner of Patents and Trademarks*